United States Patent
Tonnies

(10) Patent No.: US 7,931,642 B2
(45) Date of Patent: Apr. 26, 2011

(54) INFUSION PUMP COMPRISING A COMPUTER FOR CALCULATING THE RESPECTIVE MAXIMUM PERMISSIBLE DOSAGE

(75) Inventor: Jan G. Tonnies, Kiel (DE)

(73) Assignee: Codman Neuro Sciences Sarl, Le Lode (CH)

(*) Notice: Subject to any disclaimer, the term of this patent is extended or adjusted under 35 U.S.C. 154(b) by 812 days.

(21) Appl. No.: 10/862,543

(22) Filed: Jun. 7, 2004

(65) Prior Publication Data

US 2005/0021006 A1   Jan. 27, 2005

Related U.S. Application Data

(63) Continuation-in-part of application No. 09/787,342, filed as application No. PCT/DE99/03000 on Sep. 20, 1999, now abandoned.

(30) Foreign Application Priority Data

Sep. 18, 1998  (DE) .................................. 198 42 722

(51) Int. Cl.
*A61M 1/00*  (2006.01)
(52) U.S. Cl. .................. 604/890.1; 604/246; 604/891.1; 604/30
(58) Field of Classification Search ............ 604/65–67, 604/151–153, 246, 247, 503, 504, 506, 890.1, 604/891.1, 30
See application file for complete search history.

(56) References Cited

U.S. PATENT DOCUMENTS

| | | | |
|---|---|---|---|
| 4,392,849 A | 7/1983 | Petre et al. | |
| 4,475,901 A | 10/1984 | Kraegen et al. | |
| 4,731,051 A * | 3/1988 | Fischell | 604/67 |
| 5,010,473 A | 4/1991 | Jacobs | |
| 5,305,745 A * | 4/1994 | Zacouto | 600/324 |
| 5,421,812 A * | 6/1995 | Langley et al. | 604/6.07 |
| 5,800,387 A | 9/1998 | Duffy et al. | |
| 6,248,080 B1 * | 6/2001 | Miesel et al. | 600/561 |
| 6,986,347 B2 * | 1/2006 | Hickle | 128/200.24 |
| 2004/0193025 A1 * | 9/2004 | Steil et al. | 600/316 |

FOREIGN PATENT DOCUMENTS

WO   WO 8403218 A1   8/1984

* cited by examiner

*Primary Examiner* — Kevin C Sirmons
*Assistant Examiner* — Laura C Schell
(74) *Attorney, Agent, or Firm* — Larson & Larson, P.A.; Frank Liebenow; Justin Miller

(57) ABSTRACT

Infusion pump for the delivery of a quantity of a medicament to the body of a patient determinable by means of an electronic control device, the pump being provided with a computer for calculating the maximum permitted administration quantity for each case as a function of the previously delivered quantity and with a blocking device for preventing further administration of the medicament on exceeding a predetermined, permitted maximum value, in which the computer determines the quantity or concentration of the active substance in the body of the patient resulting from the delivered medicament quantity and its breaking down in the body and compares it with the predetermined maximum value.

6 Claims, 2 Drawing Sheets

INFUSION PUMP COMPRISING A COMPUTER FOR CALCULATING THE RESPECTIVE MAXIMUM PERMISSIBLE DOSAGE

PRIOR APPLICATIONS

This application is a continuation-in-part of Ser. No. 09/787,342 filed Mar. 16, 2001 now abandoned, a §371 U.S. National Phase application, which bases priority on International Application No. PCT/DE99/03000, filed Sep. 20, 1999, which in turn bases priority on German Application No. DE 198 42 722.0 filed Sep. 18, 1998.

BACKGROUND OF THE INVENTION

1. Field of Invention

The invention relates to an infusion pump for the delivery of a quantity of medicament to the body of a patient determinable by means of an electronic control device, the pump being provided with a computer for calculating the maximum permitted delivery quantity as a function of the previously delivered quantity and a blocking device for preventing further medicament delivery on exceeding a predetermined, permitted maximum value.

2. Description of the Prior Art

Such infusion pumps are used for supplying a patient with a medicament over a long time period and the medicament quantity continuously delivered by the infusion pump corresponding to the needs of the patient can be adjusted.

DE 33 90 462 C2 discloses an implantable infusion pump equipped with a computer, which determines the medicament quantity delivered over a "sliding time window/slot," e.g. over three hours and blocks further delivery if the quantity delivered over this time period exceeds a maximum value.

However, this procedure is inadequate and the sliding time window length random. In many cases, such as e.g. with an attack of pain, it is necessary to briefly considerably raise the quantity of active substance to be delivered by the pump in order to rapidly raise the active substance level. However, whereas a quantity distributed over three hours can be tolerated, this can prove toxic when administered over three minutes. However, an infusion rate allowed when distributed over three hours, can prove toxic or even lethal when the administration extends beyond three hours. This problem cannot be solved with the "sliding time window."

The problem of the invention is to provide an implantable infusion pump making it possible to reliably determine in each case the allowed delivery quantity.

SUMMARY OF THE INVENTION

According to the invention this problem is solved in that the computer determines the quantity or concentration of the active substance in the body of the patient on the basis of the medicament quantity delivered and its breaking down in the body and compares it with the predetermined maximum value.

A preferred embodiment is characterized in that the computer is provided with a memory storing a quantity resulting from the adding up of the delivered quantity in each case and a subtraction of the percentage of the quantity entered in the memory resulting from the expected breaking down of the medicament in the body, as well as a comparator which constantly compares the quantity entered in the memory with the predetermined, permitted maximum value.

The maximum value at which blocking takes place is consequently not, as in the case of the prior art, a value averaged out over a given time window, but is in the form of the integral reduced by the amount resulting from the half-life of the medicament over the total quantity delivered.

The computer is preferably provided with a device which, either with a time interval predetermined in accordance with the expected breaking down of the medicament in the body, brings about the subtraction of a specific percentage of the quantity entered in the memory, or in the case of a fixed, predetermined time intervals brings about the subtraction of a percentage of the quantity entered in the memory corresponding to the expected breaking down of the medicament.

In the case of the proposed construction of the infusion pump it is ensured that the administration of the medicament, which is brought about by means of the control device by the doctor or optionally also the patient, does not exceed a maximum permitted value.

In order to adjust the device for a given patient, it is merely necessary to input the half-life of the medicament to be administered and the individually permitted maximum value (toxic threshold).

It is obvious that the device must also be programmed in such a way that the lower minimum value (action threshold) is maintained.

The pump can be an implantable infusion pump. It is also possible to place the computer (or an additional, parallel-operating computer) in an external control device. It is possible for a bolus administration (namely an infusion of the medicament which in the case of long-term administration would lead to the toxic threshold being exceeded) only being possible in the case of electromagnetic coupling with the control device.

DESCRIPTION OF THE DRAWINGS

The invention is described in greater detail hereinafter relative to the drawing wherein.

DETAILED DESCRIPTION OF THE PREFERRED EMBODIMENT

Figure 1:
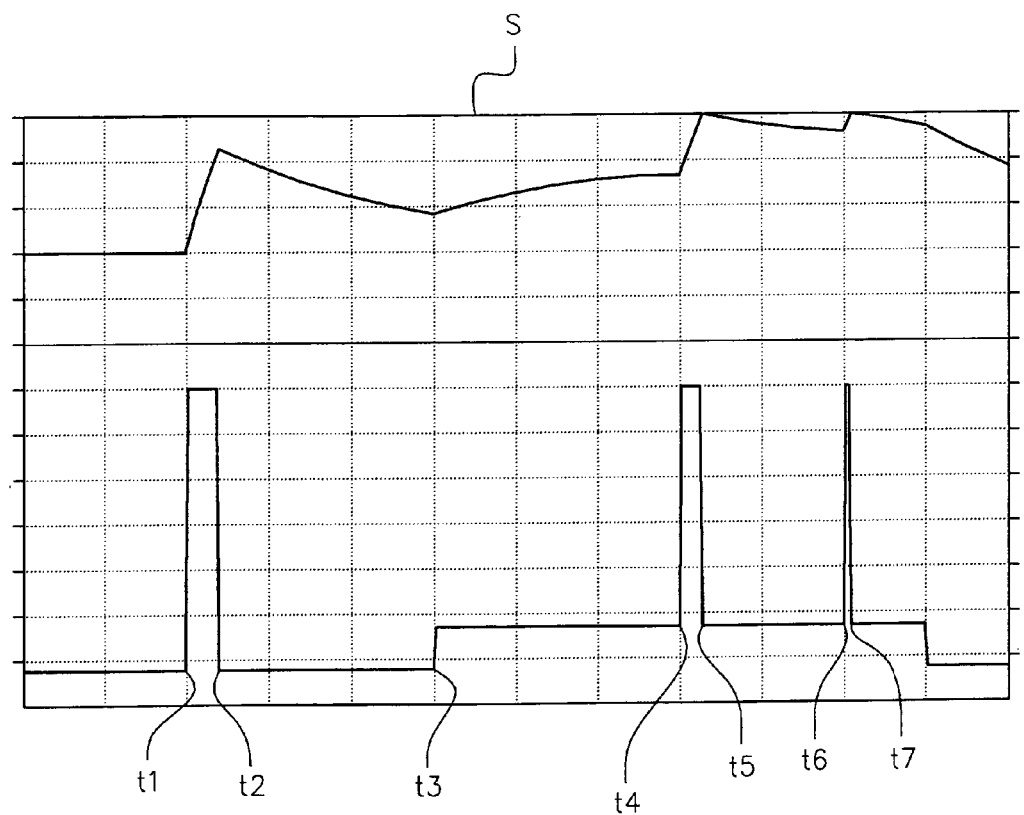
FIG. 1 shows, in the lower graph, an infusion profile and, in the upper graph, the pattern resulting from this infusion profile of the quantity entered in the memory, the expected quantity (and therefore the concentration) of the active substance in the body of the patient, as well as the predetermined, permitted maximum value (threshold S)

In the case of the infusion profile shown in FIG. 1 there is initially a long-term administration with a relatively low infusion rate. As from time t1 to t2 (caused by the patient or doctor) a first bolus administration takes place, i.e. a brief administration with a high infusion rate, such as is e.g. necessary if the patient suffers an acute attack. At time t3 switching to a higher infusion rate takes place. At time t4, using the control device, the administration of a bolus is brought about which, on reaching the predetermined threshold S is prematurely stopped at time t5 by the computer. At time t6 the user attempts to set a bolus administration, which is stopped at time t6 because the threshold S has been reached.

The path of the active substance concentration in the body of the patient resulting from this infusion profile and which is essentially proportional to the active substance quantity present in the body is shown in the lower graph.

The pattern of the active substance concentration is represented by a time integral over the infused quantity, reduced by the breaking down resulting from the half-life of the substance, i.e. as a function with a linear term determined by medicament administration and a negative exponential term determined by the medicament braking down rate.

In the drawing of FIG. 1, this leads up to time t1 to a constant path, because here the quantity supplied precisely corresponds to the quantity broken down by the body. The administration of the bolus at time t1 leads to a steep rise in the active substance concentration. At the end of bolus administration at time t2 the concentration continuously drops, because the supplied active substance quantity is lower than the broken down quantity. After doubling the infusion rate at time t3 the concentration constantly rises, but with a shallower rise.

The bringing about of a further bolus administration through the user or doctor at time t4 leads to a concentration rise up to the threshold at time t5, which at time t6 leads to an automatic termination of bolus administration by the computer. The attempt at time t7 to bring about a further bolus administration is immediately prevented by the computer due to the immediate reaching of the threshold.

The path of the active substance concentration is simulated in the computer of the implantable infusion pump (which can also be located in the control device).

In predetermined time intervals, e.g. every 10 sec, the quantity entered in the memory of the infusion pump is increased by a quantity corresponding to the amount delivered by the infusion pump in this time period. Furthermore, a mathematically determined percentage of the quantity entered in the memory is subtracted from the half-life of the delivered medicament, the resulting quantity is stored as the actual value. Alternatively, in time intervals given by the half-life (i.e. more frequently with a shorter half-life and less frequently with a longer half-life), the amount delivered in this time period can be summed and a fixed quantity subtracted.

The value entered in the memory consequently always corresponds (due to the not precisely determinable half-life this is naturally only approximately) to the actual amount in each case or concentration of the active substance in the body of the patient, whilst taking account of the breaking down thereof.

Figure 2:
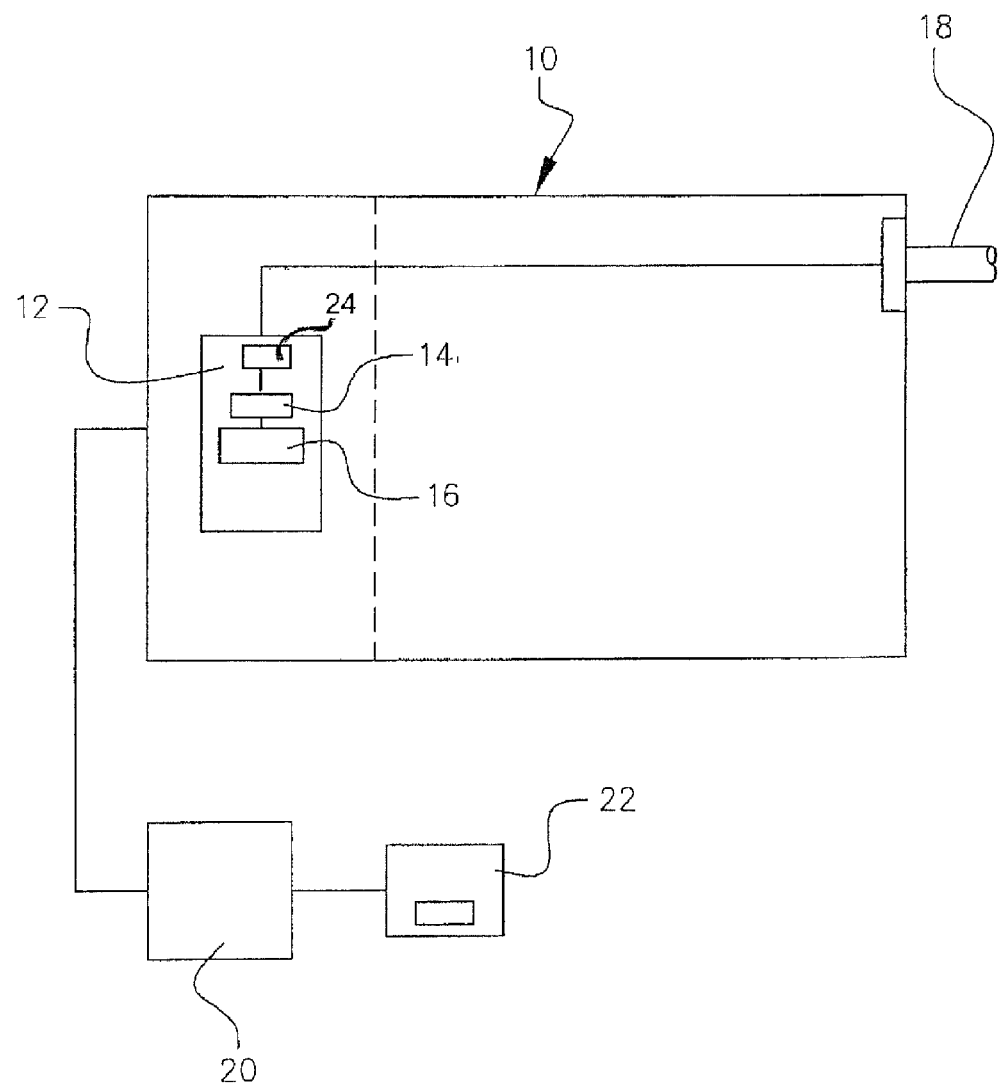
FIG. 2 illustrates an infusion pump of the present invention.

Referring to FIG. 2, an infusion pump 10 for the delivery of an amount of a medicament to a patient's body is shown. Infusion pump 10 includes a first computer 12 which acts as an electronic control device for infusion pump 10. First computer 12 has a memory 14 and a comparator 16 which controls a blocking device 18 of infusion pump 10. Within memory 14 is stored a quantitative figure (not shown) which is a result of a summation of a total delivered medicament amount and a subtracting of a percentage of a quantity entered in memory 14 resulting from an expected breaking down of the medicament in the patient's body. Comparator 16 constantly compares the quantity entered in memory 14 with a pre-determined, permissible maximum value of the medicament. Device 24 brings about a subtraction of a specific percentage of the quantity entered in the memory. Since infusion pump 10 can be implantable, it is possible to have an external control device 20. In such embodiment, as shown in FIG. 2, a second computer 22 is provided for controlling external control device 20 whereas first computer 12 controls the implantable infusion pump 10.

Equivalent elements can be substituted for the ones set forth above such that they perform in the same manner in the same way for achieving the same result.

Having thus described the invention, what is claimed and desired to be secured by Letters Patent is:

1. An infusion pump for the delivery of an amount of a medicament to the body of a patient determinable by means of an electronic control device, the infusion pump comprising:
   a) a first computer, the first computer calculating a maximum permitted quantity of the medicament to be administrated each time as a function of a previously delivered quantity and an expected breaking down rate of the medicament,
   b) a blocking device, the blocking device preventing further administration of the medicament upon exceeding a predetermined, permitted maximum value, the predetermined, permitted maximum value being a time integral over the infused quantity, reduced by a breaking down resulting from a half-life of the medicament divided by a total quantity of the medicament delivered,
   c) the first computer having a memory in which is stored a quantitative figure resulting from a summation of a total delivered medicament amount and a subtracting of a percentage of a quantity entered in the memory resulting from an expected breaking down of the medicament in the body,
   d) the first computer having a comparator which constantly compares the quantity entered in the memory with the predetermined, permitted maximum value, and
   e) the first computer having a device which, with a predetermined time interval corresponding to the expected breaking down of the medicament in the body, subtracts a fixed percentage of the quantity entered in the memory.

2. An infusion pump according to claim 1, wherein the infusion pump is implantable within the body of the patient and can be operated by an external control device.

3. An infusion pump according to claim 2, wherein the first computer operates the infusion pump and a second computer operates the external control device.

4. An infusion pump for the delivery of an amount of a medicament to the body of a patient determinable by means of an electronic control device, the infusion pump comprising:
   a) a first computer, the first computer calculating a maximum permitted quantity of the medicament to be administrated each time as a function of a previously delivered quantity and an expected breaking down rate of the medicament,
   b) a blocking device, the blocking device preventing further administration of the medicament upon exceeding a predetermined, permitted maximum value, the predetermined, permitted maximum value being a time integral over the infused quantity reduced by an amount resulting from a half-life of the medicament divided by a total quantity of the medicament delivered,
   c) the first computer having a memory in which is stored a quantitative figure resulting from a summation of a total delivered medicament amount and a subtracting of a percentage of a quantity entered in the memory resulting from an expected breaking down of the medicament in the body,
   d) the first computer having a comparator which constantly compares the quantity entered in the memory with the predetermined, permitted maximum value, and
   e) the first computer having a device which with fixed, predetermined time intervals brings about a subtraction of a percentage of the quantity entered in the memory corresponding to the expected breaking down of the medicament.

5. An infusion pump according to claim 4, wherein the infusion pump is implantable within the body of the patient and can be controlled by an external control device.

6. An infusion pump according to claim 5, wherein the first computer operates the infusion pump and a second computer operates the external control device.

* * * * *